United States Patent [19]

Jacob et al.

[11] Patent Number: 4,585,792
[45] Date of Patent: Apr. 29, 1986

[54] PROTECTIVE ADDITIVE TO VAGINAL PRODUCTS AND CATAMENIALS

[75] Inventors: Joseph Jacob; John R. Lau, both of Wooster, Ohio

[73] Assignee: Technology Unlimited Inc., West Wooster, Ohio

[21] Appl. No.: 626,304

[22] Filed: Jun. 29, 1984

Related U.S. Application Data

[63] Continuation-in-part of Ser. No. 492,022, May 5, 1983, abandoned.

[51] Int. Cl.$^4$ .................... A61K 31/34; A61K 9/24; A61K 9/26
[52] U.S. Cl. .................... 514/474; 514/967; 514/921; 424/22; 424/21
[58] Field of Search .................... 424/280, 22, 21; 514/474, 967, 921

[56] References Cited

U.S. PATENT DOCUMENTS

| | | | |
|---|---|---|---|
| 4,077,407 | 3/1978 | Theeuwes et al. | 424/19 |
| 4,160,020 | 7/1979 | Ayer et al. | 424/21 |
| 4,160,452 | 7/1979 | Theeuwes | 424/22 |
| 4,414,212 | 11/1983 | Naylor | 424/280 |

FOREIGN PATENT DOCUMENTS

2532016  2/1976  Fed. Rep. of Germany ...... 424/280

OTHER PUBLICATIONS

Tampax Insert (1982 Copyright).

*Primary Examiner*—Albert T. Meyers
*Assistant Examiner*—F. L. Abramson
*Attorney, Agent, or Firm*—Ray S. Pyle

[57] ABSTRACT

This invention relates to a method of prophylaxis with respect to Toxic Shock Syndrome in warm blooded animals, comprising the placing of a propylactically effective dosage of ascorbic acid in the vagina or in the area of the vagina.

2 Claims, No Drawings

PROTECTIVE ADDITIVE TO VAGINAL PRODUCTS AND CATAMENIALS

RELATED SUBJECT MATTER

This application is a continuation-in-part of application Ser. No. 492,022, filed May 5, 1983, now abandoned.

GENERAL DISCLOSURE

Certain bacteria when present in the human vagina produce virulent poisons called toxins. These toxins, if given entry to the blood stream, are the causative agents of Toxic Shock Syndrome (TSS). TSS is not caused by the invasion of the bacteria but by the toxin alone. One means of entry for these toxins is through ulcerations and lesions in the vaginal mucosa, although entry is not limited to mucosa disruption. One common cause of ulcerations and lesions is the use of tampons for catamenial control.

This disclosure explains the discovery that the toxins are inactivated by L-ascorbic acid. The L-ascorbic acid is topically applied by products intended for use in contact or within the vagina. These include pads, sponges, tampons, panty liners and spermicidal gels, among others. The addition of L-ascorbic acid to any or all of these products is useful in improving the health of the user by reducing the risk of TSS.

BACKGROUND OF THE INVENTION

1. Field of the Invention

This invention describes the innovative use of L-ascorbic acid as topically applied to the vaginal area during menses. The L-ascorbic acid counteracts the toxins known to contribute to Toxic Shock Syndrome.

2. Description of Prior Art

Numerous articles have been published in scientific journals as well as the popular press regarding Toxic Shock Syndrome, its symptoms and its etiology (*Surgery*, October 1981, 153:4; *Fortune*, Aug. 10, 1981).

It has been discovered that *Staphylococcus aureus*, a commonly occurring bacterium that causes serious infections in humans, existed in the vaginas of almost all the female victims of Toxic Shock Syndrome. However, it is noted that *Staphylococcus aureus* does not initiate Toxic Shock Syndrome as a result of the invasion of the intact organism into the blood stream. Instead, Staphylococcus aureus colonizes in the vaginal cavity which technically is located outside the body. As *Staphylococcus aureus* grows and multiplies, it produces at least two virulent poisons which have been identified as Pyrogenic Exotoxin C and Staphylococcal Enterotoxin F. These toxins then enter the bloodstream of the victim, by way of micro-ulcerations in the vaginal wall.

One means of entry for these toxins has been linked to the use of tampons, since tampons are known to cause ulcerations and lesions in the vaginal mucosa. *Annals of Internal Medicine*, June 1982, Vol. 96, No. 6 (Part 2) p. 855, Column 2.

We have found that only after entering the bloodstream do the toxins act systemically and elicit the symptoms associated with Toxic Shock Syndrome. These symptoms include high fever, diarrhea, vomiting and rash followed by a rapid drop in blood pressure and vital organ failure resulting in a mortality rate of approximately 6% of those who contract the disease.

SUMMARY OF THE INVENTION

This invention is the discovery that L-ascorbic acid when topically applied to the vaginal area of a human female during menses will inactivate toxins known to contribute to Toxic Shock Syndrome.

The toxin which is responsible for Toxic Shock Syndrome is essentially that produced by *Staphylococcus aureus*. There may possibly be other toxins produced by other bacteria.

The novel approach of this invention, is the focus on detoxification of the toxic product of bacteria, rather than an attempt to eliminate the bacteria.

It has been discovered, according to this invention, that L-ascorbic acid is outstandingly effective in detoxification of the toxins found in the vaginal area of a human female host. Although L-ascorbic acid is known to be a strong antioxidant, it is not known by the inventor of this approach how the L-ascorbic inactivates the toxin. Toxin structures are as yet unknown and the chemistry of this invention is unknown.

It is known, by the discovery of this invention, that the external administration of an effective amount of L-ascorbic acid to the vagina of a human female host will detoxify any toxins to the point of substantially complete elimination of the danger of Toxic Shock Syndrome.

DESCRIPTION OF THE PREFERRED EMBODIMENT

L-ascorbic acid has important properties in that the dry crystals are stable in the air for a very long period of time. However, once L-ascorbic acid enters into solution, it is capable of undergoing oxidation in a variety of reactions. The tendency of L-ascorbic acid to be oxidized increases with increasing pH ("The Antioxidant Vitamins", CRC Critical Review, *Food Sciences & Nutrition*, March 1979, pp. 271).

L-ascorbic acid is added, according to this invention, to the appropriate carrier at milligram levels, which is completely compatible with the pH of the vaginal cavity.

Although it has not been determined how L-ascorbic acid functions to detoxify bacterial toxins, it is known that L-ascorbic acid possesses relatively strong reducing power as is shown in its ability to decolorize many dyes (Merck Index, 8th ed.). These kinds of reactions may be accelerated by alkalies, iron and copper. In order to achieve the same chemical effect as L-ascorbic acid, very strong chemical reducing agents would be required.

Also, L-ascorbic acid is capable of reducing the disulfide bonds in proteins and toxins to free sulphydral groups, thus resulting in their biological inactivation (Charles E. Clark and T. J. Smith, "Effects of Ascorbic Acid (AA) on Diphtheria Toxin and Intoxicated HELA Cells," *Journal of Nutritional Science, Vitaminology*, 22 (1976) 313-319).

L-ascorbic acid has demonstrated biological activities that are capable of completely inactivating Diphtheria exotoxin in vitro (ibid) at concentrations of 90 micrograms L-ascorbic acid per milliliter. In order to achieve the same effect, strong reducing agents such as para-methylaminophenol sulfate or 2-mercaptoethanol would be required. However, compounds these would cause deleterious effects on biological tissues if administered to man.

There appears to be no known approach to TSS prevention using L-ascorbic acid. This new use of a very safe product has been discovered, according to this invention, to possess essentially full and complete prophylactic power for prevention of TSS.

EXAMPLE A

We do not know the mechanism by which L-ascorbic acid renders the stephlococcal toxins ineffective, but we are aware that L-ascorbic acid will act as a reducing agent, an antioxidant and a free radical sequestering agent. We also, from in vitro testing, know that it does inactivate the causative agents in Toxic Shock Syndrome. Therefore, it is theorized that the detoxification may be the result of the following reaction.

L-ascorbic acid is known to oxidize to dehydroascorbate from the following reaction:

FIG. 1

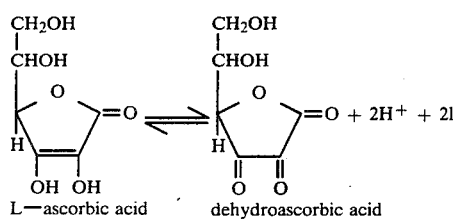

L—ascorbic acid    dehydroascorbic acid

By a series of intermediate reaction steps, a protein or toxin, may interact with the ascorbic acid and any intermediates to break the disulphide bond and produce reduced sulfhydral group. The reaction is represented as follows:

FIG. 2

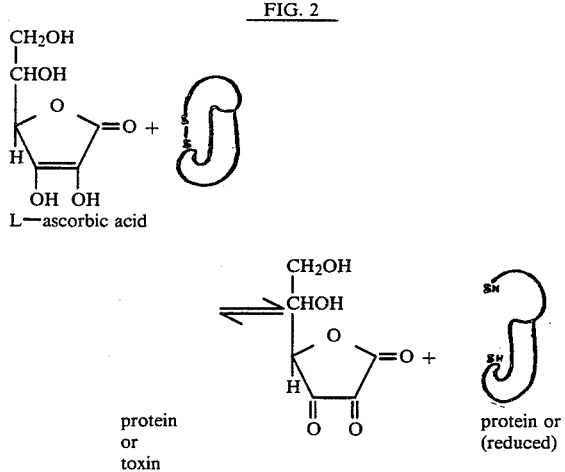

It is necessary to emphasize that this invention is a discovery and that the actual mechanism of detoxification is not yet known.

EXAMPLE B

In addition to the Staph toxins, menstrual blood contains a variety of proteins which are broken down to toxic substances. It is also possible that L-ascorbic acid plays an important role in inactivating these endogenous toxic proteins before they are absorbed into the body.

EXAMPLE C

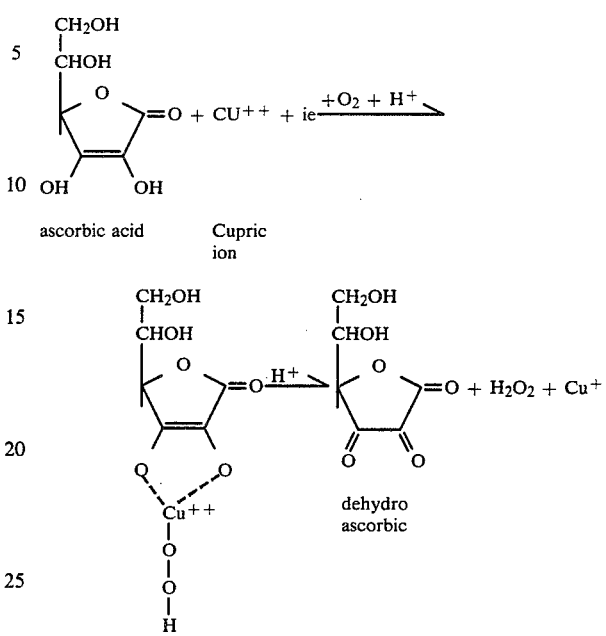

ascorbic acid    Cupric ion dehydro ascorbic

The above equations illustrate some of the important chemical reactions that participate between L-ascorbic acid, cupric++ ion and toxin.

In the foregoing disclosure there has been no reference to catalytic agents and in fact catalytic agents are believed to be unnecessary in most instances. There are sufficient metallic ions present in most environmental situations to serve any catalytic requirements of the oxidation of L-ascorbic acid. Nevertheless, in order to assure completion of the test results, and in actual commercial use it is recommended that some additional cupric++ ion be provided in order to assure a complete reaction sequence.

Again, there are many possible and unknown reactions of L-ascorbic acid and toxins, but from a careful review of the observed action according to this invention, and from extensive theoretical studies, the above effect is probably at least one of the major reactions taking place in this invention. In this reaction sequence, ascorbic acid is the reductant, and the cupric++ ion is the pro-oxidant which initiates the reaction. The cupric++ ion is reduced to the cuprous+ ion (Cu+), along with molecular oxygen. For each molecule of ascorbic acid that is oxidized to dehydroascorbate, a molecule of hydrogen peroxide is liberated. Hydrogen peroxide is a powerful oxidant when in the presence of cuprous+ ion and is capable of generating hydroxyl radicals according to the reaction below:

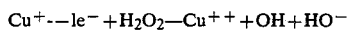

Cu+—1e−+H2O2—Cu+++OH+HO−

On the product side of the equation, the hydroxyl free radical (OH) that is formed is very reactive and is known to participate in reactions that irreversibly inactivates proteins.

It is recognized, however, that this invention is based upon laboratory observation of the inactivation of a toxin and the substantiation of such by laboratory animals. Accordingly, the above theory is supplied as the best explanation that reasonable minds conceive, but the invention herein disclosed is based upon actual tests and not on the above theory. There are a number of interrelated reaction sequences, in addition to the ones described above, that could contribute to the toxin inactivation.

EXAMPLE D

As a means for supporting the presentation made herein, a supply of Enterotoxin F was obtained from Dr. Bergdoll at the University of Wisconsin. Eighteen rabbits were injected intravenously with 10 micrograms per kilogram of body weight of the Staphylococcal Enterotoxin F. Nine of the rabbits developed severe diarrheal illness and died within 72 hours. Three additional rabbits developed severe diarrheal illness but survived. Six rabbits developed no grossly detectable signs of illness. The ten micrograms per kilogram dose therefore appears to be close to the LD 50 for this group of rabbits.

Fifteen rabbits were then injected with 10 micrograms per kilogram of the same toxin which had been preincubated for one hour at room temperature with 1.0 milligram of L-ascorbic and one micromole of $Cu^{++}$. None of the fifteen animals so challenged showed any signs of illness whatsoever.

On the basis of these data, L-ascorbic acid has demonstrated a statistically significant effect in neutralizing the Staphylococcal Enterotoxin F.

In must be emphasized that testing of this invention on a human host can never be completely conclusive for the simple reason that there is no means of predicting which person may developed TSS. However, it has been completely established that it is the toxin entering the blood stream that causes the Toxic Shock Syndrome. It is submitted that by injecting the toxin into test animals results in a complete and conclusive means for establishing the toxicity effect upon the living animal. Therefore the destruction of the toxin's ability to affect the animal is likewise fully and conclusively established.

Therefore, this invention is a prophylactic that can be safely used in substantially unlimited concentration because of its known compatibility with the human system, even in massive doses, and accordingly having been established in its ability to inactivate the causative toxins of TSS, it is safe to use on the general public as a prophylactic for the Staphylococcal Enterotoxin F.

PROTOCOL

To a solution of L-ascorbic acid prepared at a concentration of 1.0 milligram per milliliter in a 120 mM phosphate buffer pH 7.4 containing 1 mM cupric chloride, add the appropriate amount of toxin, based on a dose of 10 milligrams of toxin per kilogram of body weight, to a 1.0 ml volume solution of L-ascorbic acid, so that it can be easily injected. For example, 30 micrograms of toxin per milliliter of L-ascorbic acid solution to be administered to a 3 kilogram rabbit. This step can be accomplished using any of the soluble forms of ascorbic acid, such as the free-acid or the sodium salt. Care should be taken to keep the pH at about the 7.4 range to be compatible with intravenous injection. In addition, the solution of L-ascorbic acid should be protected from light. The crystalline form of ascorbic acid when used in commercial distribution, will not be effected by light, but in this protocol the solution should be protected from light. The toxin and the combination of toxin with ascorbate should be kept at room temperature for 1 hour to simulate time in the vagina prior to toxin absorption. At the end of that time, the entire material is injected intravenously into the rabbit.

This procedure will allow the interaction to occur between toxin molecule and the ascorbate molecule. The injection into the animal is of the entire 10 milligrams per kilogram dose of the toxin.

EXAMPLE E

In order to place the ascorbate into position to serve as an effective prophylactic, it must be placed in the area where lesions may form at the time the toxins are known to form. Accordingly, it is desirable to place the crystalline form of the ascorbate on a carrier device that may reside in the vagina during menses. The popular available tampon is an ideal carrier which requires no new technology to construct. The manner of application is simply to dust the surface of a completed tampon with the crystalline ascorbic acid. It has been found that the interstices of the wrap of the tampon is controllable to entrap the crystals of the ascorbic acid in a quantity ranging from 100 to 5,000 milligrams, and that lower quantity limit has been found to be sufficient for the the intended purpose.

The method of using the tampon as a prophylactic for the Staphylococcal toxin is to simply provide the tampon as an insertable carrier for the vagina of a human host. The L-ascorbic acid is added to the absorbent material either by surface dusting or placing a quantity of material within the body of absorbent material, and inserting the tampon carrier into the vagina during menses. It is necessary that the L-ascorbic acid be available to the cervix and vaginal mucosa of a human host in a effective amount, whether on the surface or within the body of the tampon.

EXAMPLE F

For those who do not wish to use a tampon, or possibly during light periods of menstrual fluid production near the end of the cycle, it has been found to be effective to incorporate the L-ascorbic acid with a carrier which does not have an ingredient that will in any way react with the acid.

As an example, a base of inert aqueous pharmaceutical material serves as a suitable carrier.

What is claimed:

1. A method of detoxifying the toxin produced by S. aureus in the cervix and vaginal mucosa of a human comprising the administration of a detoxifying amount of L-ascorbic acid to the cervix and vaginal mucosa by means of a menstrual tampon, said L-ascorbic acid being physically entrapped by the interstitial spaces of the tampon.

2. The method of claim 1 wherein the detoxifying amount of L-ascorbic acid is within the range of 100 mg. to 5,000 mg.

* * * * *